United States Patent [19]

Norup et al.

[11] Patent Number: 5,866,538
[45] Date of Patent: Feb. 2, 1999

[54] INSULIN PREPARATIONS CONTAINING NACL

[75] Inventors: Elsebeth Norup, Jyllinge; Liselotte Langkjær, Klampenborg; Svend Havelund, Bagsvaerd, all of Denmark

[73] Assignee: Novo Nordisk A/S, Bagsvaerd, Denmark

[21] Appl. No.: 879,991

[22] Filed: Jun. 20, 1997

Related U.S. Application Data

[60] Provisional application No. 60/020,927, Jun. 27, 1996.

[30] Foreign Application Priority Data

Jun. 20, 1996 [DK] Denmark ................... 685/96

[51] Int. Cl.$^6$ ............... A61K 38/28; C07K 14/62
[52] U.S. Cl. ............ 514/3; 530/389.2; 530/388.24; 530/303; 530/304
[58] Field of Search .................... 514/3

[56] References Cited

U.S. PATENT DOCUMENTS 4,439,181  3/1984  Blackshear et al. ............... 605/56
5,559,094  9/1996  Brems et al. ...................... 514/3

FOREIGN PATENT DOCUMENTS

WO 95/00550  1/1995  WIPO .

OTHER PUBLICATIONS

Brange J. and Langkjoer, L. Insulin Structure and stability. In: Stability and characterization of protein and peptide drugs:Case histories, Y.J.Wang, ed., Plenum Press, N.Y., p. 334, Jun. 1993.

Vinita Gupta et al., "Effect of Solvent Additives On the Thermal Stability of Insulin", Centre for Biotechnology, vol. 70., pp. 209–212.

*Primary Examiner*—Cecilia J. Tsang
*Assistant Examiner*—Michael Borin
*Attorney, Agent, or Firm*—Steve T. Zelson, Esq.; Reza Green, Esq.; Carol E. Rozek, Esq.

[57] ABSTRACT

Insulin preparations of superior chemical stability, comprising human insulin or an analogue or derivative thereof, glycerol and/or mannitol, and 5 to 100 mM of a halogenide are disclosed.

17 Claims, No Drawings

INSULIN PREPARATIONS CONTAINING NACL

INTRODUCTION

This application is a continuation of provisional application Ser. No. 60/020,927, filed Jun. 27, 1996.

The present invention relates to aqueous insulin preparations comprising human insulin or an analogue or derivative thereof, which preparations have superior chemical stability. The invention furthermore relates to parenteral formulations comprising such insulin preparations and to a method for improving the chemical stability of insulin preparations.

BACKGROUND OF THE INVENTION

Diabetes is a general term for disorders in man having excessive urine excretion as in diabetes mellitus and diabetes insipidus. Diabetes mellitus is a metabolic disorder in which the ability to utilize glucose is more or less completely lost. About 2% of all people suffer from diabetes.

Since the introduction of insulin in the 1920's, continuos strides have been made to improve the treatment of diabetes mellitus. To help avoid extreme glycemia levels, diabetic patients often practice multiple injection therapy, whereby insulin is administered with each meal.

In the treatment of diabetes mellitus, many varieties of insulin preparations have been suggested and used, such as regular insulin, Semilente® insulin, isophane insulin, insulin zinc suspensions, protamine zinc insulin, and Ultralente® insulin. As diabetic patients are treated with insulin for several decades, there is a major need for safe and life quality improving insulin preparations. Some of the commercial available insulin preparations are characterized by a fast onset of action and other preparations have a relatively slow onset but show a more or less prolonged action. Fast acting insulin preparations are usually solutions of insulin, while retarded acting insulin preparations can be suspensions containing insulin in crystalline and/or amorphous form precipitated by addition of zinc salts alone or by addition of protamine or by a combination of both. In addition, some patients are using preparations having both a fast onset of action and a more prolonged action. Such a preparation may be an insulin solution wherein protamine insulin crystals are suspended. Some patients do themselves prepare the final preparation by mixing an insulin solution with a suspension preparation in the ratio desired by the patient in question.

Human insulin consists of two polypeptide chains, the so-called A and B chains which contain 21 and 30 amino acids, respectively. The A and B chains are interconnected by two cystine disulphide bridges. Insulin from most other species has a similar construction, but may not contain the same amino acids at the positions corresponding in the chains as in human insulin.

The development of the process known as genetic engineering has made it possible easily to prepare a great variety of insulin compounds being analogous to human insulin. In these insulin analogues, one or more of the amino acids have been substituted with other amino acids which can be coded for by the nucleotide sequences. As human insulin, as explained above, contains 51 amino acid residues, it is obvious that a large number of insulin analogues is possible and, in fact, a great variety of analogues with interesting properties have been prepared. In human insulin solutions with a concentration of interest for injection preparations, the insulin molecule is present in associated form as a hexamer (Brange et al. Diabetes Care 13, (1990), 923–954). After subcutaneous injection, it is believed that the rate of absorption by the blood stream is dependent of the size of the molecule, and it has been found that insulin analogues with amino acid substitutions which counteract or inhibit this hexamer formation have an unusual fast onset of action (Brange et al.: Ibid). This is of great therapeutic value for the diabetic patient.

Pharmaceutical preparations which are based on analogues of human insulin have e.g. been presented by Heinemann et al., Lutterman et al. and Wiefels et al. at the "Frontiers in Insulin Pharmacology" International Symposium in Hamburg, 1992.

Furthermore, U.S. Pat. No. 5,474,978 discloses a rapid acting parenteral formulation comprising a human insulin analogue hexamer complex consisting of six monomeric insulin analogues, zinc ions and at least three molecules of a phenolic derivative.

Normally, insulin preparations are administered by subcutaneous injection. What is important for the patient, is the action profile of the insulin preparation which is the action of insulin on the glucose metabolism as a function of the time from the injection. In this profile, inter alia, the time for the onset, the maximum value and the total duration of action are important. A variety of insulin preparations with different action profiles are desired and requested by the patients. One patient may, on the same day, use insulin preparations with very different action profiles. The action profile requested is, for example, depending on the time of the day and the amount and composition of any meal eaten by the patient.

Equally important for the patient is the chemical stability of the insulin preparations, especially due to the abundant use of pen-like injection devices such as devices which contain Penfill® cartridges, in which an insulin preparation is stored until the entire cartridge is empty. This may last for at least 1 to 2 weeks for devices containing 1.5–3.0 ml cartridges. During storage, covalent chemical changes in the insulin structure occur. This may lead to formation of molecules which are less active and potentially immunogenic such as deamidation products and higher molecular weight transformation products (dimers, polymers, etc.). A comprehensive study on the chemical stability of insulin is given in by Jens Brange in "Stability of Insulin", Kluwer Academic Publishers, 1994.

Acta Pharmaceutica Nordica 4(4), 1992, pp. 149–158 discloses insulin preparations in which the sodium chloride concentration has been varied in the range of 0 to 250 mM. However, the major part of the preparations, including all preparations which additionally comprises glycerol, contains a rather high amount of sodium chloride, i.e. 0.7% corresponding approximately to a concentration of 120 mM. It is stated in this document that whereas sodium chloride generally has a stabilizing effect on insulin preparations, glycerol and glucose lead to increased chemical deterioration.

Surprisingly, however, it has now been shown that insulin preparations of superior chemical stability can be obtained in the presence of glycerol and/or mannitol and rather low halogenide concentrations.

DESCRIPTION OF THE INVENTION

By "analogue of human insulin" as used herein is meant human insulin in which one or more amino acids have been deleted and/or replaced by other amino acids, including non-codeable amino acids, or human insulin comprising additional amino acids, i.e. more than 51 amino acids.

By "derivative of human insulin" as used herein is meant human insulin or an analogue thereof in which at least one organic substituent is bound to one or more of the amino acids.

In the present context the unit "U" corresponds to 6 nmol.

The present invention relates to an aqueous insulin preparation comprising:

human insulin, an analogue thereof and/or a derivative thereof,
glycerol and/or mannitol, and
5 to 100 mM of a halogenide.

The above insulin preparation has a high chemical stability which e.g. is reflected in a reduction in the formation of dimers and polymers and desamido insulins after storage. Furthermore, the physical stability is not deteriorated by the presence of the rather low amount of halogenide, and the insulin does not precipitate by long-term storage of the insulin preparations.

The halogenide is preferably an alkali or alkaline earth halogenide, more preferably a chloride such as sodium chloride.

Glycerol and/or mannitol is preferably present in an amount corresponding to a concentration of 100 to 250 mM, more preferably 140 to 250 mM, even more preferably 160 to 200 mM.

The present invention is particularly advantageous in connection with preparations comprising analogues and/or derivatives of human insulin. Thus, the insulin preparation according to the invention preferably comprises one or more fast-acting analogues of human insulin, in particular analogues wherein position B28 is Asp, Lys, Leu, Val or Ala and position B29 is Lys or Pro; or des(B28–B30), des(B27) or des(B30) human insulin. The insulin analogue is preferably selected from analogues of human insulin wherein position B28 is Asp or Lys, and position B29 is Lys or Pro. The most preferred analogues are $Asp^{B28}$ human insulin or $Lys^{B28}Pro^{B29}$ human insulin.

In this embodiment, the insulin preparation preferably comprises 5 to 60 mM, more preferably 5 to 40 mM, of a halogenide.

In another embodiment the insulin preparation according to the invention comprises an insulin derivative having a protracted profile of action such as insulins having one or more lipophilic substituents. The preferred lipophilic insulins are acylated insulins, including those described in WO 95/07931 (Novo Nordisk A/S), e.g. human insulin derivatives wherein the ϵ-amino group of $Lys^{B29}$ contains an acyl substituent which comprises at least 6 carbon atoms.

The preferred insulins derivatives are the following:

B29-$N^\epsilon$-myristoyl-des(B30) human insulin, B29-$N^\epsilon$-palmitoyl-des(B30) human insulin, B29-$N^\epsilon$-myristoyl human insulin, B29-$N^\epsilon$-palmitoyl human insulin, B28-$N^\epsilon$-myristoyl $Lys^{B28}$ $Pro^{B29}$ human insulin, B28-$N^\epsilon$-palmitoyl $Lys^{B28}$ $Pro^{B29}$ human insulin, B30-$N^\epsilon$-myristoyl-$Thr^{B29}Lys^{B30}$ human insulin, B30-$N^\epsilon$-palmitoyl-$Thr^{B29}Lys^{B30}$ human insulin, B29-$N^\epsilon$-(N-palmitoyl-γ-glutamyl)-des(B30) human insulin, B29-$N^\epsilon$-(N-lithocholyl-γ-glutamyl)-des(B30) human insulin and B29-$N^\epsilon$-(ω-carboxyheptadecanoyl)-des(B30) human insulin, B29-$N^\epsilon$-(ω-carboxyheptadecanoyl) human insulin; the most preferred being B29-$N^\epsilon$-myristoyl-des(B30) human insulin.

In this embodiment, the insulin preparation preferably comprises 10 to 100 mM, more preferably 10 to 70 mM, of a halogenide.

In a particular embodiment, the insulin preparation of the invention comprises an insulin analogue as well as an insulin derivative.

In a preferred embodiment of the invention the insulin preparation comprises:

60 to 3000 nmol/ml, preferably 240 to 1200 nmol/ml, of human insulin or insulin analogue or derivative, 10 to 40 μg Zn/100 U insulin, preferably 10 to 26 μg Zn/100 U insulin, and 0 to 5 mg/ml, preferably 0 to 4 mg/ml, of a phenolic compound.

As a phenolic compound, 0.5 to 4.0 mg/ml, preferably 0.6 to 4.0 mg/ml, of m-cresol or 0.5 to 4.0 mg/ml, preferably 1.4 to 4.0 mg/ml, of phenol, or a mixture thereof, is advantageously employed.

The insulin preparation of the present invention may furthermore contain other ingredients common to insulin preparations, for example zinc complexing agents such as citrate, and phosphate buffers.

The present invention furthermore relates to a parenteral pharmaceutical formulation comprising an insulin preparation of the invention.

Moreover, the present invention is concerned with a method for improving the chemical stability of an insulin preparation comprising human insulin or an analogue or a derivative thereof, which method comprises adding glycerol and/or mannitol and 5 to 100 mM of a halogenide to said preparation.

The invention is further illustrated by the following examples which, however, are not to be construed as limiting.

EXAMPLE I

Solutions containing 100 U/ml $Asp^{B28}$ human insulin, 2.6 mg/ml phenol, 16 mg/ml glycerol and varying amounts of Zn and sodium chloride were prepared. The pH was varied in the range of 7.2 to 7.5. Stability data after 4 weeks at 37° C. are presented in the following Table 1.

TABLE 1

| μg Zn/100 U insulin | NaCl (mM) | pH | $Asp^{B28}$ Des-amido insulins formed (%) | Di- & poly-mers formed (%) |
|---|---|---|---|---|
| 13.1 | 0 | 7.2 | 3.44 | 1.35 |
|  |  | 7.5 | 3.57 | 1.36 |
|  | 5 | 7.2 | 3.48 | 1.53 |
|  |  | 7.5 | 3.31 | 1.49 |
|  | 20 | 7.2 | 2.54 | 1.72 |
|  |  | 7.5 | 2.47 | 1.26 |
| 16.3 | 0 | 7.2 | 3.35 | 1.44 |
|  |  | 7.4 | 3.41 | 1.46 |
|  | 5 | 7.2 | 1.74 | 0.95 |
|  |  | 7.5 | 2.58 | 1.38 |
|  | 20 | 7.2 | 1.91 | 1.05 |
|  |  | 7.5 | 2.00 | 1.31 |
| 19.6 | 0 | 7.2 | 3.07 | 1.57 |
|  |  | 7.5 | 2.85 | 1.80 |
|  | 5 | 7.2 | 2.71 | 1.36 |
|  |  | 7.5 | 2.24 | 1.46 |
|  | 20 | 7.2 | 1.56 | 1.15 |
|  |  | 7.5 | 1.68 | 1.13 |
| 22.8 | 0 | 7.2 | 2.71 | 2.52 |
|  |  | 7.5 | 2.34 | 1.45 |
|  | 5 | 7.2 | 2.18 | 1.95 |
|  |  | 7.5 | 1.90 | 1.19 |
|  | 20 | 7.2 | 1.51 | 1.05 |
|  |  | 7.5 | 1.46 | 1.09 |

EXAMPLE II

Insulin preparations containing dissolved $Asp^{B28}$ human insulin with varying concentrations of sodium chloride was prepared in the following way:

370.4 mg AspB28 human insulin was dissolved in water by adding 1.6 ml 0.2N HCl and 49 µl zinc chloride solution (40 mg Zn/ml). 40 g of a solution containing 40 mg/ml glycerol, 3.75 mg/g phenol and 4.30 mg/g m-cresol was added to the insulin solution while mixing. 20 g of a solution containing a) 12.0 mg/g disodium phosphate dihydrate+5 µl/g 2N sodium hydroxide, b) 12.0 mg/g disodium phosphate dihydrate+5 µl/g 2N sodium hydroxide+5 mg/g sodium chloride or c) 12.0 mg/g disodium phosphate dihydrate+5 µl/g 2N sodium hydroxide+10 mg/g sodium chloride was added while mixing. pH was adjusted to pH 7.40±0.05 and water added up to 100 ml. The $Asp^{B28}$ Human insulin preparations were introduced into Penfill® cartridges and subjected to stability tests at 25° C. and 37° C. The stability data obtained at the two different temperatures and at a phosphate concentration of 13.5 mM, 19.6 µg Zn/100 U insulin and pH=7.4 are summarized in Table 2.

TABLE 2

| NaCl added (mM) | Total conc. Of Cl⁻ (mM) | $Asp^{B28}$ Des-amido insulins formed (%) | Di- & polymers formed (%) |
| --- | --- | --- | --- |
| Data after 8 weeks at 37° C. | | | |
| 0 | 4.4 | 7.0 | 1.86 |
| 17 | 20.8 | 4.2 | 1.29 |
| 34 | 37.8 | 3.5 | 1.07 |
| Data after 8 months at 25° C. | | | |
| 0 | 4.4 | 6.4 | 1.0 |
| 17 | 20.8 | 4.1 | 0.8 |
| 34 | 37.8 | 3.7 | 0.8 |

EXAMPLE III

Insulin preparations containing dissolved $Asp^{B28}$ human insulin with varying concentrations of sodium chloride was prepared in the following way:

369.4 mg $Asp^{B28}$ human insulin was dissolved in water by adding 1.6 ml 0.2N HCl and 49 µl zinc chloride solution (40 mg Zn/ml). 40 g of a solution containing 40 mg/g glycerol, 3.75 mg/g phenol and 4.30 mg/g m-cresol was added to the solution while mixing. 10 g of a solution containing 24.0 mg/g disodium phosphate dihydrate and 11 µl/g 2N sodium hydroxide was added while mixing. Finally varying amounts (0 g to 4.38 g) of a solution containing 40 mg/g sodium chloride were added while mixing up to a sodium chloride concentration mentioned in Table 4. pH was adjusted to 7.40±0.05 and water added up to 100 ml. The $Asp^{B28}$ Human insulin preparations were introduced into Penfill® cartridges and subjected to stability tests at 25° C. and 37° C. The stability data obtained at the two different temperatures and at a phosphate concentration of 13.5 mM are summarized in Table 3.

TABLE 3

| NaCl added (mM) | Total conc. of Cl⁻ (mM) | $Asp^{B28}$ Des-amido insulins formed (%) | Di- & polymers formed (%) |
| --- | --- | --- | --- |
| Stability data after 6 weeks at 37° C. | | | |
| 5 | 8.5 | 4.1 | 0.99 |
| 12.5 | 16.3 | 3.6 | 0.92 |
| 20 | 23.8 | 3.0 | 0.87 |
| 25 | 28.8 | 3.0 | 0.82 |
| 30 | 33.8 | 2.8 | 0.80 |

TABLE 3-continued

| NaCl added (mM) | Total conc. of Cl⁻ (mM) | $Asp^{B28}$ Des-amido insulins formed (%) | Di- & polymers formed (%) |
| --- | --- | --- | --- |
| Stability data after 12 weeks at 25° C. | | | |
| 0 | 3.8 | 2.7 | 0.36 |
| 5 | 8.5 | 2.3 | 0.32 |
| 12.5 | 16.3 | 1.8 | 0.39 |
| 20 | 23.8 | 1.7 | 0.39 |
| 25 | 28.8 | 1.8 | 0.38 |
| 30 | 33.8 | 1.7 | 0.38 |

EXAMPLE IV

Insulin preparations containing dissolved $Asp^{B28}$ human insulin with varying concentrations of phosphate and sodium chloride was prepared in the following way:

375.7 mg $Asp^{B28}$ human insulin was dissolved in water by adding 1.6 ml 0.2N HCl and 49 µl zinc chloride solution (40 mg Zn/ml). 20 g of a solution containing 80 mg/g glycerol, 7.50 mg/g phenol and 8.60 mg/g m-cresol was added to the solution while mixing. Varying amounts (3.71 g to 6.71 g) of a solution containing 24.0 mg/g disodium phosphate dihydrate and 11 µl/g 2N sodium hydroxide was added while mixing, finally varying amounts (0 g to 3.65 g) of a solution containing 40 mg/g sodium chloride were added while mixing so as to obtain a sodium chloride concentration mentioned in table 6. pH was adjusted to pH 7.40±0.05 and water added up to 100 ml. The $Asp^{B28}$ Human insulin preparations were introduced into Penfill® cartridges and subjected to stability tests at 25° C. and 37° C. The stability data at the two different temperatures and three different phosphate concentrations and at 19.6 µg Zn/100 U insulin and pH=7.4 are summarized in Tables 4, 5 and 6.

TABLE 4

| NaCl added (mM) | Total conc. of Cl⁻ (mM) | Phosphate conc. (mM) | $Asp^{B28}$ Des-amido insulins formed (%) | Di- & polymers formed (%) |
| --- | --- | --- | --- | --- |
| Data after 6 weeks at 37° C. | | | | |
| 0 | 3.8 | 5 | 4.7 | 1.4 |
| 5 | 8.8 | 5 | 3.7 | 1.3 |
| 10 | 13.8 | 5 | 3.4 | 1.2 |
| 15 | 18.8 | 5 | 3.1 | 1.1 |
| 20 | 23.8 | 5 | 2.7 | 1.1 |
| 25 | 28.8 | 5 | 3.0 | 0.9 |
| Data after 12 weeks at 25° C. | | | | |
| 0 | 3.8 | 5 | 2.2 | 0.5 |
| 5 | 8.8 | 5 | 1.7 | 0.4 |
| 10 | 13.8 | 5 | 1.5 | 0.4 |
| 15 | 18.8 | 5 | 1.4 | 0.4 |
| 20 | 23.8 | 5 | 1.3 | 0.4 |
| 25 | 28.8 | 5 | 1.3 | 0.4 |

TABLE 5

| NaCl added (mM) | Total conc. of Cl⁻ (mM) | Phosphate conc. (mM) | $Asp^{B28}$ Des-amido insulins formed (%) | Di- & polymers formed (%) |
| --- | --- | --- | --- | --- |
| Data after 6 weeks at 37° C. | | | | |
| 0 | 3.8 | 7 | 4.3 | 1.2 |
| 5 | 8.8 | 7 | 3.6 | 1.2 |

TABLE 5-continued

| NaCl added (mM) | Total conc. of Cl⁻ (mM) | Phosphate conc. (mM) | Asp$^{B28}$ Des-amido insulins formed (%) | Di- & polymers formed (%) |
|---|---|---|---|---|
| 10 | 13.8 | 7 | 3.1 | 1.1 |
| 15 | 18.8 | 7 | 3.1 | 1.0 |
| 20 | 23.8 | 7 | 2.9 | 1.0 |
| 25 | 28.8 | 7 | 2.8 | 1.1 |
| Data after 12 weeks at 25° C. | | | | |
| 0 | 3.8 | 7 | 2.0 | 0.5 |
| 5 | 8.8 | 7 | 1.7 | 0.4 |
| 10 | 13.8 | 7 | 1.4 | 0.4 |
| 15 | 18.8 | 7 | 1.5 | 0.4 |
| 20 | 23.8 | 7 | 1.4 | 0.4 |
| 25 | 28.8 | 7 | 1.3 | 0.4 |

TABLE 6

| NaCl added (mM) | Total conc. of Cl⁻ (mM) | Phosphate conc. (mM) | Asp$^{B28}$ Des-amido insulins formed (%) | Di- & polymers formed (%) |
|---|---|---|---|---|
| Data after 6 weeks at 37° C. | | | | |
| 0 | 3.8 | 9 | 4.9 | 1.2 |
| 5 | 8.8 | 9 | 4.0 | 1.1 |
| 10 | 13.8 | 9 | 3.7 | 1.0 |
| 15 | 18.8 | 9 | 3.5 | 1.0 |
| 20 | 23.8 | 9 | 3.5 | 1.0 |
| 25 | 28.8 | 9 | 3.1 | 0.9 |
| Data after 12 weeks at 25° C. | | | | |
| 0 | 3.8 | 9 | n.d. | 0.4 |
| 5 | 8.8 | 9 | 1.8 | 0.4 |
| 10 | 13.8 | 9 | 1.5 | 0.4 |
| 15 | 18.8 | 9 | 1.5 | 0.4 |
| 20 | 23.8 | 9 | 1.6 | 0.4 |
| 25 | 28.8 | 9 | 1.4 | 0.4 |

EXAMPLE V

Solutions containing 0.6 mM B29-N$^\epsilon$-myristoyl-des(B30) human insulin, 1.5 or 4.0 mg/ml phenol, 5 mM sodium phosphate, 13.1 µg/ml Zn, and varying amounts of sodium chloride and mannitol were prepared. pH was adjusted to 7.4. Stability data (formation of dimers and polymers) after storage at 25° C. for 13 weeks or 37° C. for 8 weeks are presented in the following table 7.

TABLE 7

| NaCl (mM) | Mannitol (mg/ml) | Phenol 1.5 mg/ml | Phenol 4.0 mg/ml |
|---|---|---|---|
| | | Di- & polymers (%) formed after 8 weeks at 37° C. | |
| 20 | 31 | 0.77 | 0.77 |
| 50 | 22 | 0.71 | 0.71 |
| 75 | 13 | 0.65 | 0.70 |
| 100 | 5 | 0.66 | 0.68 |
| | | Di- & polymers (%) formed after 13 weeks at 25° C. | |
| 20 | 31 | 0.40 | 0.42 |
| 50 | 22 | 0.35 | 0.37 |
| 75 | 13 | 0.34 | 0.39 |
| 100 | 5 | 0.31 | 0.37 |

EXAMPLE VI

Solutions containing 0.6 mM B29-N$^\epsilon$-myristoyl des(B30) human insulin, 1.5 mg/ml phenol and 1.72 mg/ml m-cresol, 16 mg/ml glycerol or 36 mg/ml mannitol, 13.1 µg/ml Zn, 7 mM sodium phosphate and varying amounts of sodium chloride were prepared. pH was adjusted to 7.5. Stability data (formation of dimers and polymers) after storage at 25° C. for 13 weeks or 37° C. for 8 weeks are presented in the following table 8.

TABLE 8

| NaCl (mM) | Glycerol 16 mg/ml | Mannitol 36 mg/ml |
|---|---|---|
| | Di- & polymers (%) formed after 8 weeks at 37° C. | |
| 5 | 2.55 | 2.28 |
| 10 | 2.25 | 1.90 |
| 20 | 1.82 | 1.61 |
| 30 | 1.83 | n.d. |
| 40 | 1.78 | 1.56 |
| 50 | 1.68 | n.d. |
| | Di- & polymers (%) formed after 13 weeks at 25° C. | |
| 5 | 1.08 | 1.05 |
| 10 | 0.98 | 0.84 |
| 20 | 0.80 | 0.71 |
| 30 | 0.80 | n.d. |
| 40 | 0.79 | 0.70 |
| 50 | 0.72 | n.d. |

We claim:

1. A pharmaceutical formulation comprising:
    a polypeptide selected from the group consisting of human insulin, an analogue thereof, a derivative thereof, and combinations of any of the foregoing;
    glycerol, mannitol, or glycerol and mannitol; and
    5 to 100 mM of a halogenide.

2. A pharmaceutical formulation according to claim 1, wherein the halogenide is an alkali or alkaline earth halogenide.

3. A pharmaceutical formulation according to claim 1, wherein said glycerol or mannitol is present at a concentration of 100 to 250 mM.

4. A pharmaceutical formulation according to claim 1, wherein said polypeptide is an analogue of human insulin selected from the group consisting of: (i) an analogue wherein position B28 is Asp, Lys, Leu, Val or Ala and position B29 is Lys or Pro; and (ii) des(B28–B30), des(B27) or des(B30) human insulin.

5. A pharmaceutical formulation according to claim 4, wherein said polypeptide is an analogue of human insulin wherein position B28 is Asp or Lys, and position B29 is Lys or Pro.

6. A pharmaceutical formulation according to claim 4, wherein said polypeptide is des(B30) human insulin.

7. A pharmaceutical formulation according to claim 1, wherein said halogenide is present at a concentration of 5 to 60 mM.

8. A pharmaceutical formulation according to claim 1, wherein said polypeptide is a derivative of human insulin having one or more lipophilic substituents.

9. A pharmaceutical formulation according to claim 8, wherein the insulin derivative is selected from the group consisting of B29-N$^\epsilon$-myristoyl-des(B30) human insulin, B29-N$^\epsilon$-palmitoyl-des(B30) human insulin, B29-N$^\epsilon$-myristoyl human insulin, B29-N$^\epsilon$-palmitoyl human insulin, B28-N$^\epsilon$-myristoyl Lys$^{B28}$Pro$^{B29}$ human insulin, B28-N$^\epsilon$-palmitoyl-Lys$^{B28}$Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$-(N-palmitoyl-γ-glutamyl)-des(B30) human insulin, B29-N$^\epsilon$(N-lithocholyl- γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

10. A pharmaceutical formulation according to claim 9, wherein the insulin derivative is B29-N$^\epsilon$-myristoyl-des (B30) human insulin.

11. A pharmaceutical formulation according to claim 8, wherein said halogenide is present at a concentration of 10 to 100 mM.

12. A pharmaceutical formulation according to claim 1, comprising an insulin analogue as well as an insulin derivative.

13. A pharmaceutical formulation according to claim 1, wherein said polypeptide is present at a concentration of 60 to 3000 nmol/ml.

14. A pharmaceutical formulation according to claim 1, further comprising:

10 to 40 ug Zn/100 U insulin.

15. A pharmaceutical formulation according to claim 1, further comprising:

0 to 5 mg/ml of a phenolic compound.

16. A pharmaceutical formulation according to claim 15, comprising:

0.5 to 4.0 mg/ml of m-cresol or 0.5 to 4.0 mg/ml of phenol, or a mixture thereof.

17. A pharmaceutical formulation according to claim 1, wherein the halogenide is sodium chloride.

* * * * *

UNITED STATES PATENT AND TRADEMARK OFFICE
CERTIFICATE OF CORRECTION

PATENT NO. : 5,866,538
DATED : February 2, 1999
INVENTOR(S) : Norup et al.

It is certified that error appears in the above-identified patent and that said Letters Patent is hereby corrected as shown below:

Col. 1, line 22: delete "continuos" and insert --continuous--

Signed and Sealed this

Fifteenth Day of June, 1999

Attest:

Q. TODD DICKINSON

Attesting Officer     Acting Commissioner of Patents and Trademarks